United States Patent [19]

Tschakaloff

[11] Patent Number: 5,290,281
[45] Date of Patent: Mar. 1, 1994

[54] SURGICAL SYSTEM

[75] Inventor: Alexander Tschakaloff, Hamburg, Fed. Rep. of Germany

[73] Assignee: Medicon eG, Tuttlingen, Fed. Rep. of Germany

[21] Appl. No.: 898,453

[22] Filed: Jun. 15, 1992

[51] Int. Cl.$^5$ .............................................. A61F 5/04
[52] U.S. Cl. ........................................ 606/28; 606/77; 606/69; 219/229
[58] Field of Search ................ 219/229, 233, 240; 606/27, 28, 29, 30, 60, 69, 72, 73, 76, 77

[56] References Cited

U.S. PATENT DOCUMENTS

| | | |
|---|---|---|
| 1,609,920 | 12/1926 | Whited . |
| 2,472,144 | 6/1949 | Calhoun ........................ 219/228 X |
| 2,547,437 | 4/1951 | Bunts et al. . |
| 3,494,364 | 2/1970 | Peters . |
| 3,851,145 | 11/1974 | Fukanaga . |
| 3,900,714 | 8/1975 | Beyer ................................ 219/229 |
| 4,060,089 | 11/1977 | Noiles . |
| 4,074,110 | 2/1978 | Slaughter . |
| 4,093,491 | 6/1978 | Whelpton et al. . |
| 4,186,448 | 2/1980 | Brekke . |
| 4,428,376 | 1/1984 | Mericle . |
| 4,484,055 | 11/1984 | Haines et al. . |
| 4,523,591 | 6/1985 | Kaplan et al. . |
| 4,539,981 | 9/1985 | Tunc . |
| 4,645,503 | 2/1987 | Lin et al. . |
| 4,696,300 | 9/1987 | Anderson . |
| 4,724,839 | 2/1988 | Bedi et al. . |
| 4,898,186 | 2/1990 | Ikada et al. . |
| 4,903,691 | 2/1990 | Heinl . |
| 4,905,680 | 3/1990 | Tunc ........................... 606/69 |
| 4,944,742 | 7/1990 | Clemow et al. . |
| 4,959,065 | 9/1990 | Arnett et al. ........................ 606/69 |
| 4,986,875 | 1/1991 | Hamlin, Jr. . |
| 5,108,399 | 4/1992 | Eitenmuller et al. ................. 606/77 |
| 5,169,400 | 12/1992 | Mühling et al. ....................... 606/77 |

FOREIGN PATENT DOCUMENTS

| | | | |
|---|---|---|---|
| 13862 | 8/1980 | European Pat. Off. .............. 606/69 |
| 0260222 | 3/1988 | European Pat. Off. . |
| 0266146 | 5/1988 | European Pat. Off. . |
| 290138 | 11/1988 | European Pat. Off. ............. 606/69 |
| 0390613 | 10/1990 | European Pat. Off. . |
| 3914163 | 8/1990 | Fed. Rep. of Germany ........ 606/69 |
| 9007304 | 7/1990 | World Int. Prop. O. . |

OTHER PUBLICATIONS

Catalogue published by SYNTHES, section entitled Implants, pp. 2-1 through 2-635, 1991.
Technical Publication published by VDI-Richtlinien pertaining to Screws made from Thermoplastics, pp. 1-19, 1973.

*Primary Examiner*—Peter A. Aschenbrenner
*Attorney, Agent, or Firm*—Reed Smith Shaw & McClay

[57] ABSTRACT

A surgical system including: (1) a thermoplastic, body absorbable, bodily tissue fixation plate having a plurality of formations and a plurality of through-bores arranged in alternating relation along with plate; (2) body absorbable fasteners adapted for insertion into the through-bores to secure the plate to underlying bodily tissue; and (3) heating apparatus including a wand having a heating tip of a configuration adapted to substantially matingly cooperate with the formations to facilitate heating and bending of the plate into conformance with the underlying bodily tissue.

18 Claims, 4 Drawing Sheets

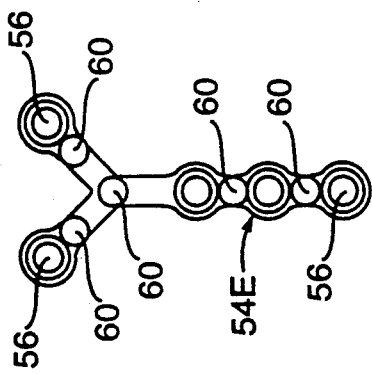
FIG. 6E
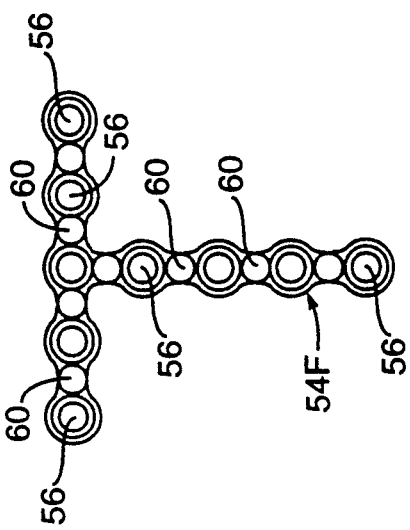
FIG. 6D
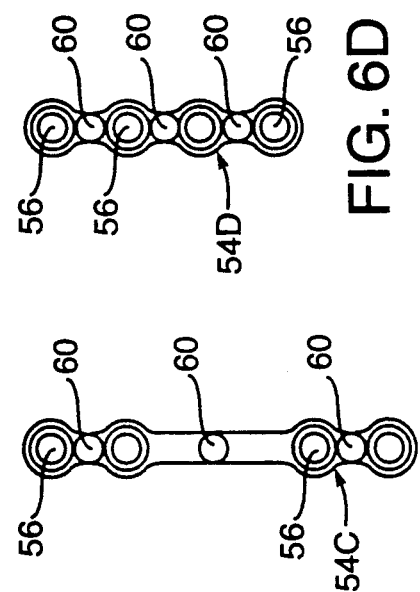
FIG. 6F
FIG. 6C
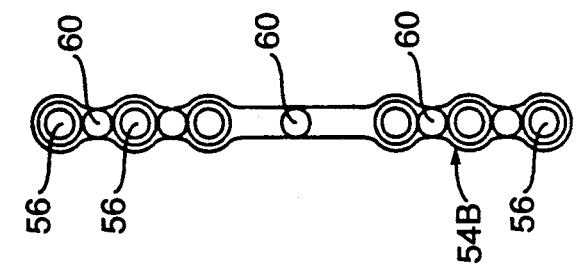
FIG. 6B
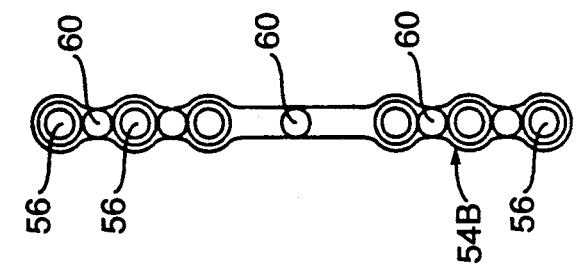
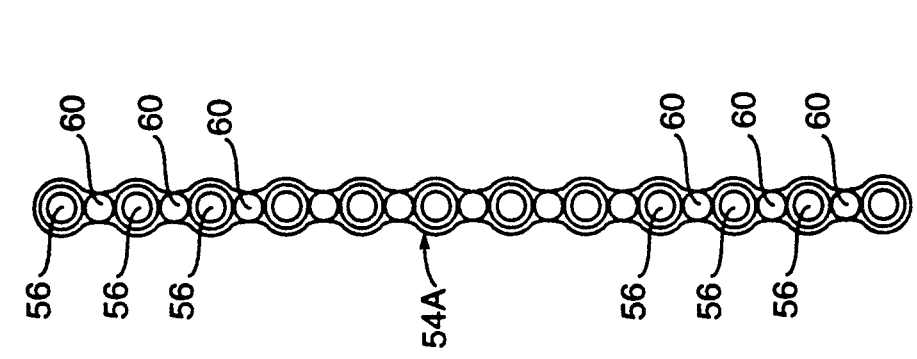
FIG. 6A

SURGICAL SYSTEM

FIELD OF THE INVENTION

The present invention relates generally to surgical equipment and systems and, more particularly, to bodily tissue fixation systems including bodily tissue fixation hardware comprising biocompatible, biodegradable and body-absorbable (resorbable) thermoplastic plates and fasteners for securing the plates to bodily tissue for fixation thereof, and heating apparatus for bending and shaping the plates, in situ, without damaging surrounding biological tissue.

BACKGROUND OF THE INVENTION

Perhaps the most well known and widely used bodily tissue fixation systems typically employ metallic hardware, e.g., plates, screws, rods and the like, formed of biocompatible, corrosion resistant metals such as titanium and stainless steel. While such systems are generally effective for their intended purposes, they possess a number of inherent shortcomings. For example, for some surgical treatments it is not feasible to remove the hardware once it is implanted. As a result, the patient must permanently carry within his body substances foreign to his natural bodily tissue. In other situations wherein it is desirable or necessary to remove the hardware, a second surgical operation is required to perform such removal. Further, when using metallic fixation plates, to secure severed bone material, or the like, the inherent rigidity of the plates does not readily permit the plates to be adequately bent so as to closely conform to bone areas of small radii of curvature, such as cranial and facial bones, particularly those of children. As a consequence, optimum restraint of the bones against relative movement is not always achieved and the strength and/or appearance of the mended area, when healed, may not be entirely satisfactory.

In efforts to overcome some of the encumbrances of metallic bodily tissue fixation systems, an assortment of body absorbable bodily tissue fixation hardware and systems have been proposed, for example, in U.S. Pat. Nos. 4,905,680, 4,903,691, 4,539,981, 4,523,591, German Patentschrift DE 39 143 163, European Patent No. 0 260 222 and WIPO 90/07304.

U.S. Pat. Nos. 4,905,680 and 4,903,691 describe, in particular, bone fixation plates formed of body absorbable plastic material provided with a plurality of bores through which fasteners such as screws are inserted whereby the fasteners enter the bone to fasten the plate across a severed or fractured bone area in order to fixate the bone to promote stabilization during healing thereof. Although satisfactory for use in fixing severed bone areas of generally linear configuration (such as the elongated bones of the limbs) the bone plates taught in U.S. Pat. No. 4,905,680, by being relatively rigid similar to the previously discussed metallic plates, are not particularly well adapted to securing severed bone areas which may have small radii of curvature such as cranial and facial bones, especially those of a small child. That is to say, the plates cannot readily be brought into close conformance with highly curved bone areas whereby those areas may be effectively restrained against relative movement as is required to achieve rapid, sturdy and non-disfiguring mending of the bone.

German Patentschrift DE 39 143 163 discloses a bone fixation system comprising a body absorbable thermoplastic plate which is reinforced by carbon fibers and heated by an electromagnetic radiation heating means to cause the plate to soften and conform to the severed bone being repaired. Upon satisfactory conformance of the plate to the bone, the plate is then secured to the bone by suitable screws, or the like. While this system may serve to effectively restrain the bones being fixated from relative movement, two of the preferred means it may employ to heat the plate, i.e., either an infrared or a microwave radiation generator, if not cautiously operated, can cause irradiation of surrounding bodily tissue to a degree sufficient to overheat and thereby destroy the tissue. Moreover, the microwave or infrared generator heats the entire plate at once, which may not always be desired or necessary and which could render the plate too liquefied and structurally incoherent to be of any practical use, unless the surgeon exercises vigilant and continuous monitoring of the physical status of the plate during heating thereof. Also, the carbon fiber used for reinforcing the plate may not be fully biocompatible with and absorbable by the patient's body.

German Patentschrift DE 39 143 163 also teaches that the heating means may heat electrically conductive fibers in the plate by induction heating. Again, however, great care must be exercised so as not to heat the plate to a degree which would destroy its structural integrity and efficacy.

European Patent No. 0 260 222 teaches the concept of securing severed bone segments together by means of covering the severed area with flexible, body-absorbable plastic material and securing the material to the bone segments via body absorbable fasteners such as screws or rivet-like members. Aside from providing limited restraint against relative movement of the bone segments, the system taught therein requires bores of several millimeters to be provided in the bone to receive the fasteners. Such large diameter bores and fasteners may be acceptable for many bone repair situations but, due to their size, they limit the practical application of the system essentially to repair of relatively large bones. In fact, the screws are of such dimensions that they require a central longitudinal passage of sufficient size to internally receive along the full length thereof an elongated screwdriver shaft to drive the screw into the bone. The presence of the central longitudinal passage thus necessarily requires the screw to be of an unacceptably large diameter for small bone repair operations. The screw is further provided with a plurality of transverse flow passages in communication with the central passage so as to enable the necessary body fluid to enter the interior of the screw and effect decomposition of the screw not only from the exterior but the interior thereof as well. Hence, because of the physical dimensions of the screws, without the existence of the interconnected longitudinal and transverse passages, the time required for decomposition of the screws would be substantially increased, perhaps undesirably prolonging the bone healing process.

An advantage exists, therefore, for a body-absorbable bodily tissue fixation plate whereby the plate (such as a bone fixation plate) can be molded to closely conform to the shape of the bodily tissue being fixated. Such plate should be thermoplastic and readily bendable through the application of a series of spot heatings at predetermined sites thereon via appropriate heating apparatus without potentially sacrificing the physical integrity of the plate.

A number of apparatus for localized heating applications are known. One such device is the conventional hand-held, electrical resistance soldering iron commonly used to solder small-scale electrical or mechanical connections. The primary disadvantage of this sort of device, if it were somehow attempted to be utilized in a surgical operation of the type contemplated herein, is that its elongated heating element, which operates at high temperature along the entire length thereof, is quite likely to come into contact and burn the skin or other biological tissue of the patient and possibly the operator, particularly if the surgery is being performed in a rather deep surgical incision.

In this connection, U.S. Pat. Nos. 3,494,364 and 4,074,110 describe heating apparatus for, inter alia, cauterizing biological tissue in surgical operations. The heating apparatus disclosed in these references include heating wands having tips that are heated by electrical resistance in the case of U.S. Pat. No. 3,494,364 and conduction in the case of U.S. Pat. No. 4,074,110. In each of these patents, the wands include housings which do not lend themselves well to working in either deep incisions or small scale operations because their bulk precludes clear vision of the area being treated. U.S. Pat. No. 3,494,364 describes, for example, a heating wand housing having an outer diameter of approximately three-eighths of an inch, which, as will be appreciated later herein, is over three times the diameter of the heating wand of the present invention.

Moreover, the heating tips taught by these references saliently project from their respective wands and are substantially (as in U.S. Pat. No. 3,494,364) or entirely (as in U.S. Pat. No. 4,074,110) uninsulated. As a consequence, biological tissue in the vicinity of the treatment area is exposed to a material risk of being inadvertently damaged by the heating tips.

High frequency radiation heating apparatus may also be used for localized heating. However, if such apparatus are used to heat materials in close proximity to living tissue, the surrounding living tissue behaves like a dielectric heating material, i.e., the energy generated by the high frequency heating apparatus is diffused three-dimensionally throughout the surrounding body tissue at a rate and magnitude of heat transference which are related to the dielectric constants of the body tissue. Consequently, such methods and apparatus are quite difficult to control in terms of preventing tissue burn in delicate surgical operations.

Ultrasonic heating apparatus represent yet another potential means for localized heating. However, ultrasonic heating apparatus suffer from related disadvantages as those attendant to infrared or microwave radiation heating apparatus (discussed hereinabove in connection with German Patentschrift DE 39 143 163). That is to say, the thermoplastic plate and/or the biological tissue in the immediate vicinity of the treatment area, if the ultrasonic energy is not carefully controlled, may rapidly become exposed to an energy level sufficient to overheat and destroy the plate and, possibly, the immediately surrounding biological tissue.

Laser heating apparatus have achieved wide acceptance as surgical apparatus for cauterizing biological tissue. The heating energy produced by a specific laser is related to the type of element or compound whose atoms are stimulated to produce the laser beam. For example, a $CO_2$ laser produces a beam in the infrared range having a wavelength of approximately 10.6 $\mu$m, an Nd:YAG laser produces a beam also in the infrared range and has a wavelength of approximately 1.06 $\mu$m, and an Argon laser produces a yellowish green to blue beam of approximately 0.455 $\mu$m–0.515 $\mu$m.

In surgical applications, laser energy is typically applied to the biological tissue being treated in short bursts rather than a continuous beam because the high intensity of most surgical laser beams is such that, if continuously applied, the laser light would eventually vaporize the area being treated.

The surgeon would have to invest a great deal of time and effort in becoming and remaining skilled in how to effectively apply the laser energy to the desired areas of the plastics contemplated to be employed by the present invention without overexposing the plastics or the surrounding bodily tissue to the intense laser energy. Further, laser equipment is somewhat unattractive from the perspectives of cost, maintenance and storage.

Surgical laser heating apparatus, even if hand-held are also rather cumbersome to use in that they normally require a complex system of mirrors and/or fiber optic cables contained in a bulky housing, thereby rendering it difficult to accurately direct the laser energy to the desired treatment area, particularly if the area being treated is deep within the patient's body. Additionally, surgical laser apparatus are expensive and they are normally rather difficult to sterilize.

Cauterizing forceps whose opposed tongs are connected to sources of electrical potential are also known. In the operation of these devices, a quantity of biological tissue is grasped by the tongs and high frequency electrical energy is conducted between the tongs through the biological tissue to selectively cauterize the tissue. As noted previously, however, control of the diffusion of the high frequency energy is difficult and tissue in the vicinity of the grasped tissue may become unintentionally cauterized by this procedure, especially if the forceps are inserted into a relatively deep surgical incision.

Additionally, cauterizing forceps are not effective in heating plastic because plastic is a poor conductor of electricity. A frequency generator in the gigahertz range would normally be required in order to produce the energy sufficient to heat absorbable plastic bone fixation plates of the types contemplated herein, but the expense such a generator would be prohibitive since the present cost of such equipment ranges from about thirty thousand to about fifty thousand U.S. dollars. Moreover, the frequencies produced by a gigahertz frequency generator could cause interference with other electrical equipment operating in the vicinity of the generator.

An advantage thus exists for a hand-held heating apparatus adapted for highly localized heating, particularly for surgical treatment applications, that is easily handled and sterilizable, that will not burn or otherwise damage biological tissue in the vicinity of the treatment area, and that can be accurately monitored and controlled.

SUMMARY OF THE INVENTION

In accordance with the present invention, there is provided a surgical system including equipment particularly adapted for fixating fractured or severed bones, or for affixing a ligament, tendon or connective tissue to a bone to promote rapid and beneficial healing of the treated bones and/or tissues.

Even more particularly, the present invention includes a heating apparatus constructed for precise in situ heating and shaping of fixation plates, straps, or the like, formed of body absorbable thermoplastic materials (which also form part of the present invention), while minimizing the likelihood of damage to surrounding biological tissue. The heating apparatus comprises a thin, elongated, hand-held wand which is heated only at its tip by electrical resistance heating. The tip electrically connects an inner electrode and an outer electrode that surrounds and extends coaxially with the inner electrode. The materials and dimensions of the inner and outer electrodes are so selected and designed as to minimize space yet assure that the tip is capable of being rapidly heated while the outer electrode remains essentially cool to the touch.

In a preferred application thereof, the heating apparatus cooperates as part of a surgical system with one or more specially configured plates fabricated from body absorbable thermoplastic material which are heated, in situ, by the tip of the heating apparatus as the plates are secured by the surgeon via a plurality of screws or similar fasteners to a bone, cartilage, tendon, connective tissue or other bodily tissue being fixated. The tip of the heating apparatus is configured to substantially mate with one or more strategically located formations of truncated, substantially concave spherical shape provided on the plates whereby the heating tip does not slip relative to the formations during heating of the plate (so that the potential for accidental damage to surrounding bodily tissue is reduced) while the arrangement of the formations enable the plate to be softened by the heating apparatus such that the plate can be bent with minimal force to closely conform to the configuration of the bodily tissue being fixated. In a presently preferred embodiment, the tip is approximately 3 mm in diameter and assumes a truncated, substantially convex spherical shape including a radius of curvature (approximately 1.5 mm) adapted to substantially mate with the formations provided on the plates. However, it is further contemplated that if necessary, the tip may be manufactured to a diameter less than 3 mm and its radius of curvature less than 1.5 mm, depending upon the dimensions of the plate and its associated heating tip accommodating formations.

The heating apparatus additionally comprises a source of electric power and may be operated by a hand switch, a foot switch, of the like, and preferably includes an adjustable tip temperature control. The apparatus is also preferably provided with temperature sensing means in communication with an audible and/or visual indicator means for notifying the operator that the tip has reached a temperature suitable for enabling in situ softening, bending and shaping of a selected one of virtually any known physiologically absorbable plastic material.

The system of the present invention thus offers, inter alia, a hand-held heating apparatus of slender design and relatively inexpensive manufacture which is easy to manipulate and sterilize. Additionally, the heating apparatus is so constructed that the likelihood of damage to biological tissue in the vicinity of the thermoplastic body absorbable plate being shaped in situ is minimal (particularly if the plate includes, as in accordance with a further aspect of the present invention, formations adapted to substantially mate with the shape of the heating tip of the heating apparatus), including instances wherein the heating tip of the apparatus is inserted into deep surgical incisions.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein:

FIGS. 6A, 6B, 6C, 6D, 6E and 6F represent plan views of several presently preferred embodiments of bodily tissue fixation plates of the surgical system of the present invention.

DETAILED DESCRIPTION OF THE INVENTION

Figure 1:
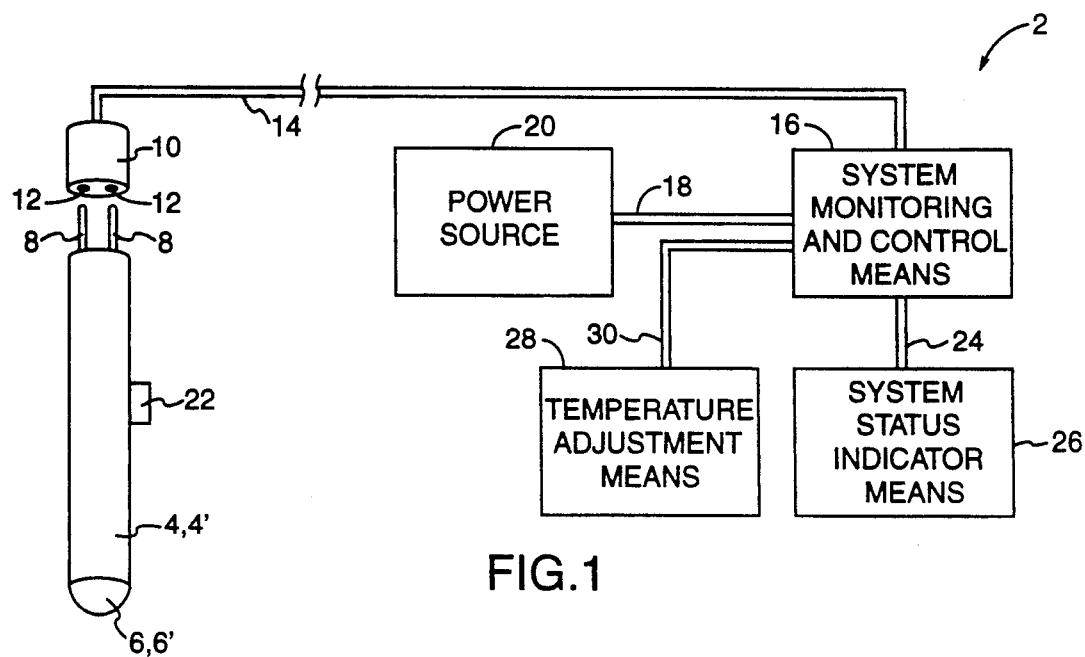
FIG. 1 is a schematic representation of a heating apparatus for use in the surgical system of the present invention.

With reference to FIG. 1, there is illustrated a schematic diagram of a heating apparatus 2 for use in the surgical system of the present invention. The heating apparatus 2 includes a heating wand (two presently preferred embodiments of which will be described in greater detail hereinafter and referenced by numerals 4 and 4', respectively) of elongated substantially cylindrical configuration which carries at one end thereof a heating tip 6 or 6'. The opposite end of the wand 4,4' is preferably releasably connectable as by suitable electrical connector means of known construction, for example, a plurality of male connectors 8 to a receiving plug 10 having a plurality of female sockets 12 corresponding in number, diameter and arrangement to the male connectors 8. The plug 10 is in turn respectively connected via conductor means 14 to a system monitoring and control means 16, which is connected by conductor means 18 to a power source 20. Although it is preferred to wand 4,4' be generally straight in shape throughout its length, as shown, it is also contemplated that the end of the wand carrying the heating tip 6,6' may be angled relative to the remainder of the shaft of the wand, if such is desired. Moreover, it is further possible to provide the exterior of the wand with means for enhancing the user's gripping in order to minimize slipping of the wand from the user's grasp during manipulation of the wand in the performance of a surgical operation.

Power source 18 may comprise any suitable source of AC or DC power and control of the flow of electrical therefrom to the wand 4,4' may be accomplished by any suitable switch means including, but not limited to, a button switch 22 provided on the wand or other suitable means such as a foot-pedal switch (not illustrated).

System monitoring and control means 20 preferably comprises a central processing unit (CPU) in the form of a microprocessor having suitable integrated circuitry, as is known in the art, for receiving a detected signal indicative of a condition (in the present system a signal indicative of the temperature of the heating tip 6,6'), comparing the detected signal to a nominal condition signal and transmitting a system status signal via circuitry 24 to means for indicating the status of the system, such as system status indicator means 26. A temperature adjustment means 28 also operates as a component of the heating apparatus 2. Temperature adjustment means 28 comprises an adjustable temperature control which communicates via circuitry 30 with system monitoring means 20 to establish the nominal condition signal representative of temperature against which the signal indicative of heating tip temperature (which signal is transmitted by way of suitable circuitry carried by conductor means 14) is compared. Temperature adjustment means 28 is preferably adjustable to establish a nominal condition corresponding to essentially any temperature within the range of temperatures at which the bodily tissue fixation plates of the present invention may be softened. When the nominal condition signal and the detected symbol indicative of heating tip temperature substantially coincide, system monitoring and control means 20 transmits a system status signal via circuitry 24 to a system status indicator means 26 which audibly (such as by a tone, a simulated voice signal or the like) and/or visually (such as by activation of a light source, a printed message, or the like) informs the surgeon that the heating tip has attained a temperature corresponding to the melting temperature of the fixation plate. This comparing of the detected signal and nominal condition signal thereafter is performed continuously throughout the treatment in order to maintain the preselected melting temperature.

According to the invention, the presently preferred body absorbable thermoplastic materials forming the bodily tissue fixation plates (the compositions of which will be later described in greater detail) can be softened, bent and shaped, depending upon their compositions at temperatures ranging from about 40° C. (for generally amorphous materials) to about 250° C. (for generally crystalline materials). Accordingly, temperature adjustment means 28 is desirably adjustable to establish a nominal condition within system monitoring and control means 20 corresponding to a melting temperature anywhere in the general range of about 40° C. to about 250° C.

Hence, upon activation of switch means 22 power is supplied not only to the wand 4,4' (to commence heating of the heating tip 6,6') but also to system monitoring and control means 20 through circuitry 18 as well as the temperature adjustment means 28 and the system status indicator means 26 (the latter two components being supplied with power through their electrical communication via circuitry 30 and 24, respectively, with system monitoring and control means 20). Once the heating tip 6,6' attains the appropriate threshold temperature as determined by the coincidence of the heating tip temperature signal and the nominal condition signal, the system monitoring and control means 20 transmits a system status signal to system status indicator means 26 which causes same to inform the surgeon that the heating tip is ready for use whereby the surgeon may then begin to apply heat to the plate to be melted in order to bend the plate. As the surgery progresses, should the heating tip temperature signal be found by the system monitoring and control means to be indicative of an excessive heating tip temperature, the system monitoring and control means ceases transmission of power to wand 4,4'. Simultaneously, system monitoring and control means 20 transmits a signal to system status indicator means 26 causing same to inform the surgeon that the heating tip is not in a condition ready for use. Once the heating tip has cooled sufficiently, the system monitoring and control means 20 reestablishes transmission of power to the wand and transmits a signal to system status indicator means 26 to inform the surgeon that the wand is again ready for use. This automatic monitoring and control of the system occurs continuously throughout the surgical procedure.

Figure 2:
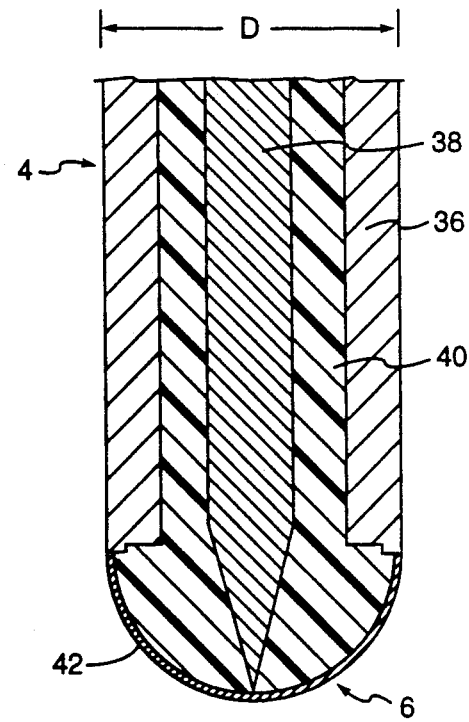
FIG. 2 is an enlarged section view, in elevation, of a preferred embodiment of a portion of a heating wand of the heating apparatus shown in FIG. 1.

Turning to FIG. 2, there is shown an enlarged section view of a preferred embodiment of a heating wand 4 of the heating apparatus 2 for use in the surgical system of the present invention. The wand 4 includes a generally cylindrical metallic tube 36 having an outer diameter D of approximately 3 mm which acts as a first current carrying electrode and a metallic wire 38 having a sharpened point extending longitudinally and internally of the tube 36 which acts as a second current carrying electrode. The tube 36 and a sharpened tip of the wire 38 are electrically connected with respective ones of the connectors 8 (FIG. 1) in a manner known to those skilled in the art. The wire and tube are insulated and physically spaced from one another by suitable electrical and thermal insulation material 40 such as epoxy resin, or the like. The insulation material protruding from the distal and of the tube 36 is ground or otherwise suitably shaped to produce a convex radius of curvature for the tip of the wand 4 of approximately 1.5 mm. A very thin layer of metal 42 (approximate 1 μm thickness) is then sputtered, steamed or otherwise suitably applied to the convex wand tip so as to electrically connect the sharpened point of the wire 38 with the tube 36, which metal layer 42 serves as the heating tip 6 of the wand 4.

The heating wand 4,4' preferably operates under a voltage of approximately one volt, a current of about one ampere and the heating energy of the tip 6,6' is approximately one watt. Such energy is sufficient to heat the tip 6,6' to the temperatures required to soften the thermoplastic bodily tissue fixation plates contemplated herein. However, due to the relatively minimal voltage and current, a surgeon holding the shaft of the wand 4,4' senses neither an elevated temperature in nor electrical flow through the wand shaft. Thus, a heating wand is provided having a shaft which remains essentially cool to the touch and electrically shock-free during operation. The heating tip is of truncated, convex spherical shape and presents a small heating surface area which is particularly adapted to matingly cooperate with formations provided on bodily tissue fixation plates to be later described. So configured, the potential for damage to bodily tissue surrounding the treatment area is minimized, even in surgical operations performed in relatively deep incisions.

The metal layer 42 simultaneously serves as a heating element and as its own temperature sensor. More particularly, the system monitoring and control means 20 continuously monitors the electrical resistance of the metal layer 42 (in relation to its resistance at a reference temperature such as room temperature) throughout a surgical operation, and via mathematical analysis operations known in the art, which operations are programmed into the memory of the system monitoring and control means 20, the working temperature of the tip 6 can be continuously deduced which, in turn, causes the system monitoring and control means to transmit appropriate control signals to system status indicator means 26 and/or wand 4 in the manner described hereinabove.

In accordance with this embodiment, heat distribution over the tip 6 is inhomogenous. That is, the central region thereof in the vicinity of wire 38 operates at a higher temperature than outer peripheral regions located generally closer to tube 38. An unexpected advantage of such a heat distribution is that the cooler peripheral regions serve to arrest "diving" of the tip 6 into the bodily tissue fixation plates contacted thereby which virtually assures that the plates will not be destroyed by the heating tip. Further, a heating tip having this pattern of heat distribution can, because of the stabilizing effect of the cooler peripheral regions thereof, be held into contact with the plate somewhat longer than perhaps heating tip 6' of wand 4' to be described hereinafter, whereby a more uniform heating of the entire thickness of the plate may be achieved.

Figure 3:
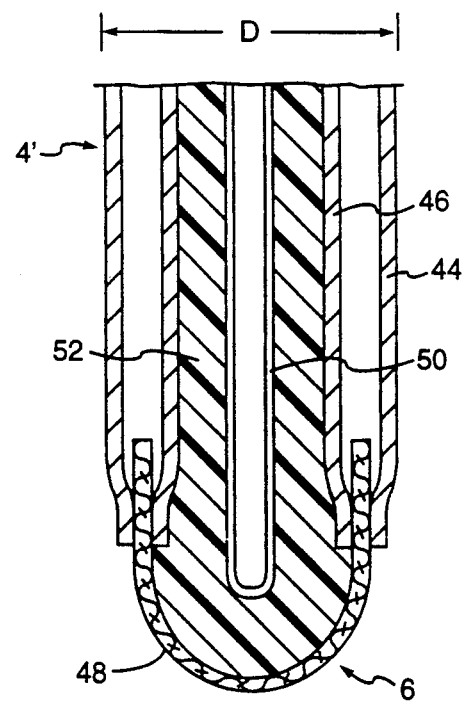
FIG. 3 is an enlarged section view, in elevation, of a further preferred embodiment of a portion of a heating wand of the heating apparatus of the present invention.

FIG. 3 represents the construction of a further preferred embodiment of the heating wand of the present invention, herein designated by reference numeral 4', which is designed for localized heating of bodily tissue fixation plates of a type which will be described later herein and which form another component of the instant surgical system. Heating wand 4' comprises a first generally cylindrical metallic tube 44 and interiorly and substantially concentric therewith a second generally cylindrical metallic tube 46, wherein tubes 44 and 46 are electrically connected to respective ones of connectors 8 (FIG. 1). As with tube 36 of wand 4, tube 44 preferably has an outer diameter D of approximately 3 mm.

Fixedly clamped between the distal ends of metallic tubes 44 and 46 is an electrically conductive fabric or similar material 48 preferably including a quantity of carbon fibers or other substance suitably adapted to retain heat. Concentric with and positioned internally of tube 46 is a temperature probe 50 which also is connected to a designated connector 8, it being understood that receiving plug 10 is provided with a socket 12 to accommodate the connector associated with the temperature probe 50. Thermally and electrically insulative material 52 such as epoxy resin isolates temperature probe 50 from inner tube 46 and the electrically conductive fabric 48. The heating tip 6', like heating tip 6 of wand 4, is formed to a radius of curvature of approximately 1.5 mm.

Figure 4:
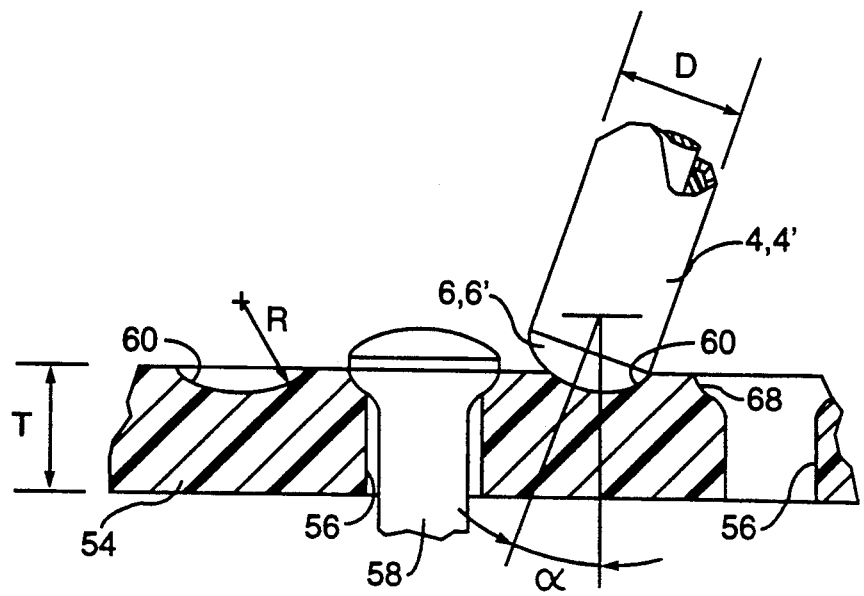
FIG. 4 is an enlarged view, in partial section, of a heating wand constructed according to the present invention in contact with a bodily tissue fixation plate, which plate forms a further aspect of the instant invention.

FIG. 4 depicts a heating wand 4,4' as it would be employed during a surgical operation. The heating tip 6,6' thereof is shown in contact with and applying heat to a thermoplastic, biodegradable and body absorbable, bodily tissue fixation plate 54 constructed in accordance with a preferred embodiment of the present invention. Plate 54 may be formed of any suitable biocompatible plastic material known in the art generally having a softening temperature of between about 40° C. and about 250° C. Examples of such materials may include, but should not be construed to be limited to, polylactide, polyglycolides, polycaprolactane, poly (orthoesters) and the like as well as copolymers of the same, which possess favorable in vivo strength and absorption characteristics and which may be either unreinforced or reinforced with similar or other suitable body absorbable materials.

Plate 54, a number of contemplated geometries of which will be described later herein in connection with FIGS. 6A–6F, is desirably of a thickness T of less than about 2 mm and includes a plurality of spaced apart through-bores 56 adapted to accommodate fastener means 58 which preferably assume the form of screw-type fasteners. Fasteners 58 are also formed from any suitable biocompatible and body absorbable plastic material from the classes listed above with regard to plate 54 or from other acceptable materials of similar properties and characteristics. Situated between adjacent through-bores 56, except where a through-bore is a terminal bore generally proximate an end of the plate 54, are formations 60 adapted to substantially matingly cooperate with the heating tip 6,6' of wand 4,4' during a plate heating and bending procedure. That is, formations 60 preferably are configured as depressions of truncated, substantially concave spherical shape having a radius of curvature R of preferably no greater than about 1.5 mm. Hence, when heating tip 6,6' is in contact with plate 54 as shown in FIG. 4, the matingly cooperative shapes of the heating tip and the formations prevent the heating tip from slipping from the plate during heating of the plate. The benefits arising from this relationship include more precise and rapid heating of the plate 54 and a reduced potential for accidental damage to surrounding bodily tissue.

Further, because of the mating partially spherical shapes of the heating tip 6,6' and formations 60, the wand 4,4' does not have to be maintained at or substantially near to a right angle with respect to the plate 54 during a plate bending procedure. As shown in FIG. 4, the wand 4,4' may be tilted through an angle $\alpha$ of approximately 20° and still maintain mating contact of 35 tip 6,6' with formation 60. Consequently, this arrangement not only enhances the surgeon's ability to more clearly see the treatment area, it additionally furnishes the surgeon with a substantial range of motion within which to manipulate the wand 4,4', an advantage in instances where it may be difficult if not impossible to orient the wand essentially perpendicular to the upper surface of the plate.

Figure 5:
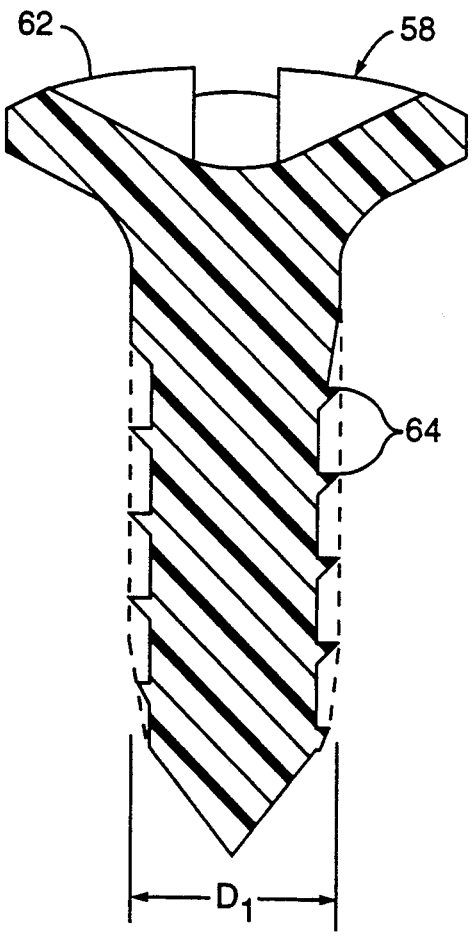
FIG. 5 is an enlarged section view, in elevation, of a fastener according to a further aspect of the present invention for securing a bodily tissue fixation plate to underlying bodily tissue.

FIG. 5 shows an enlarged section view of a screw fastener 58 according to the present invention for fastening the plate 54 to underlying bodily tissue during a surgical operation. As suggested hereinabove, screw 58 may be formed of any suitable biodegradable and biocompatible plastic material; however, the material must be chosen from those materials having sufficient hardness whereby the screw head 62 and screw threading 64 do not fail upon the application of torque to the screw head as occurs when fastening the bodily tissue fixation plate to underlying bodily tissue. Although, the tool-receiving portion of screw head 62 may assume any conventional socket configuration, it is preferred that the screw head include a socket shape adapted to minimize the likelihood of inadvertent slippage of the torquing tool or screw driver during screw turning, such as, for example, a Phillips-type socket. Moreover, the underside of the screw head 62 is desirably contoured as at 66 to conform to the shape of a screw head seat 68 formed at the upper ends of through-bores 56 of plate 54 (FIG. 4) whereby the screw fastener/plate height profile is minimized, thereby enhancing the surgeon's ability to access formations 60 with the heating tip 6,6'. It is preferred that the distal end of the threaded portion of the screw fastener 58 be formed into a generally pointed configuration as illustrated so as to facilitate guidance and insertion of the fastener into both its corresponding through-bore 56 and the preformed receiving hole therefor, to be described later herein, provided in the underlying bodily tissue being fixated.

Additionally, the outer thread diameter $D_1$ of the threading 64 of screw fastener 58 of the present invention is desirably less than about 2.0 mm. Indeed, according to presently preferred embodiments thereof, the outer threading diameter is typically approximately 1.4 mm or less for normal service requirements and up to about 1.8 mm for emergency requirements, and the corresponding nominal bore diameter of through-bores 56 is preferably about 1.9 mm or less. Because of the very small diameters of the screw fasteners 58, they are particularly well-suited for reparation of small and/or non-weight bearing bones or other bodily tissues and can be relatively rapidly absorbed by the body without need of adsorption enhancement measures such as the interconnected flow passages of the screws disclosed in European Patent No. 0 260 222. Further, although preferably assuming the configurations of screws, it is contemplated that the fasteners of the present invention may be formed into other shapes such as pins, rivets, and the like.

FIGS. 6A-6F represent several views of preferred configurations of bodily tissue fixation plates of the present invention, herein designated by reference numerals 54A-54F. The plates may assume generally linear shapes as in FIGS. 6A-6D, a Y-shape as in FIG. 6E, a T-shape as in FIG. 6F or other shapes such as X-shaped, cross-shaped or still more elaborate forms.

Figure 7A:
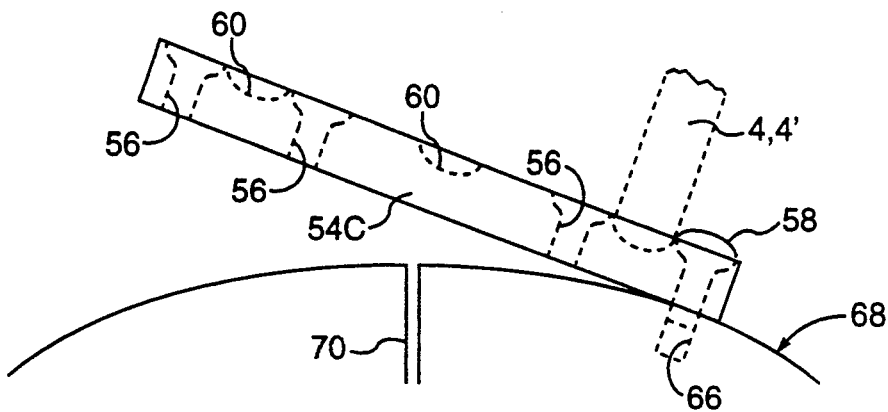
FIGS. 7A, 7B and 7C depict a sequential installation of a bodily tissue fixation plate of the present invention onto a severed area of bodily tissue for fixation thereof.
Figure 7B:
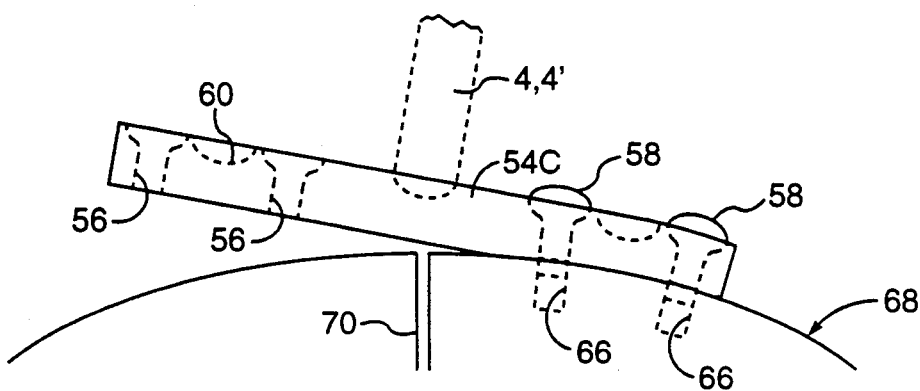
Figure 7C:
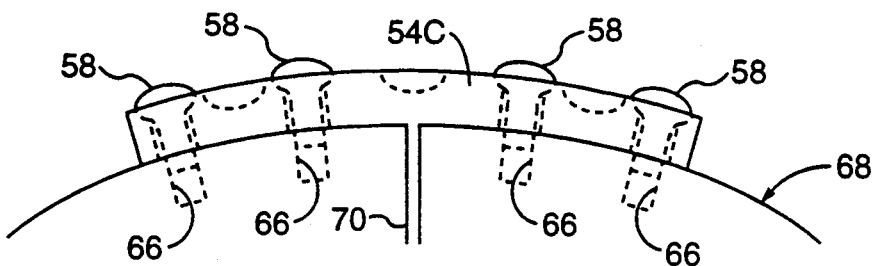

FIGS. 7A-7C depict a plate installation sequence using the combination of components discussed hereinabove which together constitute the surgical system according to the present invention. In FIG. 7A, a bodily tissue fixation plate configured in accordance with plate 54C of FIG. 6C is shown anchored by a first screw 58 extending through a first through-bore 56 of plate 54C, which screw is threaded into a drilled and preferably tapped hole 66 in bodily tissue such as bone 68 which is shown by reference numeral 70, as being severed or fractured. With the plate so anchored, the heating tip of heating wand 4,4' is then inserted into a first concave formation and held therein for a few seconds to soften the plate 54C at which time the surgeon removes the heating wand and applies slight force to the plate 54C to cause the lower surface thereof to come into conformance with bone 68 and the bottom of the next adjacent through-bore 56 to contact the bone. The surgeon thereupon inserts a drill of appropriate diameter through the next through-bore, drills a second hole 66 in the bone 68, withdraws the drill, taps the hole and drives a second screw into the bone through the second through-bore 56 (FIG. 7B). This process is repeated until a screw 58 is inserted through each of the bores 56 to firmly anchor the plate 54C to the severed or fractured bone 68 as shown in FIG. 7C. To further enhance the structural integrity and strength of implant, the heating tip 6,6' can be applied to the juncture sites of the screw heads and the plate to soften and fuse the thermoplastic material of the screws with that of the plate.

Because the plate 54C, or any other plate 54 configuration contemplated by the present invention, can be incrementally and sequentially heated and shaped in situ using wand 4,4', the plate can be brought into virtual conformance with the underlying bodily tissue being fixated, including damaged tissue having small radii of curvature such as cranial and facial bones, especially those of a small child. As a result, the bodily tissue on opposite sides of the severance or fracture 70 is effectively restrained against relative movement whereby rapid, sturdy and non-disfiguring mending of the bodily tissue is achieved. Further, the heating apparatus 2 continuously monitors the wand heating tip temperature during a surgical operation so that the heating tip does not heat and soften the bodily tissue fixation plates to a state of unworkability. And, the small surface area of the heating tip and its manner of matingly cooperating with the receiving formations 60 provided on the plates 54 serve to minimize heat-related damage to biological tissue in the immediate vicinity of the treatment area, even in rather deep biological incisions.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A surgical system comprising:
    a thermoplastic, body absorbable, bodily tissue fixation plate having at least one depression thereon;
    body absorbable means for fastening said plate to bodily tissue; and
    heating apparatus including a wand having a heating tip of a truncated, substantially convex spherical shape adapted to substantially matingly cooperate with said at least one depression.

2. The system of claim 1 wherein said fastening means comprise screw fasteners.

3. The system of claim 2 wherein said screw fasteners include threading having an outer threading diameter of no greater than about 2.0 mm.

4. The system of claim 3 wherein said outer threading diameter is no greater than about 1.4 mm.

5. The system of claim 1 wherein said plate includes a plurality of through-bores wherein said fastening means are insertable into said through-bores.

6. The system of claim 5 wherein said at least one depression is situated between a pair of said through-bore.

7. The system of claim 5 wherein said at least one depression comprises a plurality of depressions.

8. The system of claim 7 wherein said through-bores and said depressions are arranged in alternating relation along said plate.

9. The system of claim 1 wherein said at least one depression has a truncated, substantially concave spherical shape.

10. The system of claim 9 wherein the radius of curvature of said heating tip and the radius of curvature of said at least one depression are substantially equal.

11. The system of claim 1 wherein the radius of curvature of said heating tip and the radius of curvature of said at least one depression are no greater than about 1.5 mm.

12. The system of claim 11 wherein said heating wand comprises a substantially cylindrical member having an outer diameter of no greater than about 3 mm.

13. The system of claim 12 wherein said heating wand comprises a first electrical conductor operating as a first electrode, a second electrical conductor operating as a second electrode, insulating material isolating said first and second conductors and formed into said truncated, substantially convex spherical shape at said heating tip, and electrically conductive material covering said heating tip and electrically connecting said first and second conductors.

14. The system of claim 13 wherein said electrically conductive material comprises a metal layer coating said heating tip.

15. The system of claim 13 wherein said electrically conductive material comprises an electrically conductive fabric.

16. The system of claim 12 wherein said heating wand further comprises an internal temperature probe.

17. The system of claim 1 wherein said heating apparatus further comprises means for adjusting the temperature of said heating tip, means for indicating a temperature status of said heating tip, and means for monitoring the temperature of said heating tip in relation to a predetermined heating tip temperature established by said means for adjusting and for controlling heating of said heating tip and operation of said means for indicating a temperature status in response to monitored heating tip temperature.

18. A method of installing a thermoplastic, body absorbable, bodily tissue fixation plate to bodily tissue, said plate including a plurality of through-bores for receiving fasteners for attaching said plate to said bodily tissue and a plurality of depressions arranged in alternating relation with said through-bores along said plate, said method comprising the steps of:
  (a) securing said plate to said bodily tissue with a first of said fasteners inserted through a first of said through-bores;
  (b) heating one of said depressions with a heating tip of a heating apparatus wand, said heating tip having a truncated, substantially convex spherical shape adapted to substantially matingly cooperate with said depressions;
  (c) bending said plate to conform to said bodily tissue;
  (d) securing said plate to said bodily tissue with another of said fasteners inserted through another of said through-bores; and
  (e) sequentially repeating steps (b) through (d) until said plate is secured to said bodily tissue via fasteners inserted through substantially all available ones of said through-bores.

* * * * *